United States Patent
Ishizuka

(10) Patent No.: US 6,736,772 B2
(45) Date of Patent: May 18, 2004

(54) ENDOSCOPE SUITABLE FOR AUTOCLAVING

(75) Inventor: Tatsuya Ishizuka, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/931,847

(22) Filed: Aug. 17, 2001

(65) Prior Publication Data

US 2002/0072653 A1 Jun. 13, 2002

(30) Foreign Application Priority Data

Aug. 28, 2000 (JP) ........................................ 2000-257723

(51) Int. Cl.⁷ ............................................... A61B 1/012
(52) U.S. Cl. ........................ 600/133; 600/130; 600/156
(58) Field of Search ................................. 600/130, 133, 600/139, 128, 140, 156

(56) References Cited

U.S. PATENT DOCUMENTS 4,616,631 A * 10/1986 Takahashi .................... 600/139
4,756,303 A * 7/1988 Kawashima et al. ......... 600/139
4,782,819 A * 11/1988 Adair .......................... 600/133
4,799,474 A * 1/1989 Ueda ........................... 600/133
5,876,331 A * 3/1999 Wu et al. ..................... 600/139

FOREIGN PATENT DOCUMENTS

JP        2-58401        4/1990

* cited by examiner

Primary Examiner—John P. Leubecker
(74) Attorney, Agent, or Firm—Scully, Scott, Murphy & Presser

(57) ABSTRACT

An endoscope suitable for autoclaving in accordance with the present invention has a barrier that separates an interior from an exterior. When the barrier is located at a predetermined position, consideration is taken into a displacement of the barrier between the position of the barrier observed before start of autoclaving and the position thereof observed after completion of the autoclaving during which predetermined pressure is applied and a thermal load is imposed.

8 Claims, 5 Drawing Sheets

ENDOSCOPE SUITABLE FOR AUTOCLAVING

This application claims the benefit of Japanese Application No. 2000-257723 filed in Japan on Aug. 28, 2000 the contents of which are incorporated by this reference.

BACKGROUND OF THE INVENTION

1. Field of the Invention

The present invention relates to an endoscope capable of undergoing autoclaving (sterilization with high-temperature high-pressure steam) when the endoscope must be disinfected or sterilized after being used.

2. Description of the Related Art

Endoscopes are widely employed in the field of medicine these days. The endoscope has an elongated insertion member inserted into a body cavity for the purpose of observing a deep region in the body cavity, or the endoscope is used in combination with a therapeutic instrument, if necessary, to perform a cure or remedy. For the medical-purpose endoscope, it is essential to reliably disinfect or sterilize a used endoscope.

Recently, autoclaving (sterilization with high-temperature high-pressure steam) is getting mainstream in sterilization of medical equipment. This is because autoclaving is no labor-intensive but low-cost, and medical equipment can be used immediately after it is autoclaved.

Typical conditions for autoclaving are stipulated in the U.S. standard ANSI/AAMI ST37-1992 recommended by the American National Standards Institute and published from the Association for the Advancement of Medical Instrumentation. The standard stipulates that, for example, a pre-vacuum sterilization process should be performed at 132° C. for 4 min and a gravity settling sterilization process should be performed at 132° C. for 10 min.

The above environmental conditions for autoclaving are quite severe for endoscopes that are precision electronic apparatuses. In order to realize an endoscope that withstands the environment to undergo autoclaving, unlike an endoscope that shall be reused after subjected to a general disinfecting or sterilizing means, various measures must be taken against high pressure, high temperature, steam, and so on.

Moreover, an existing endoscope has push-button switches such as remote control switches, which are used to control the actions of external units placed outside the endoscope, exposed on a control section thereof. For example, a push-button switch described in Japanese Unexamined Utility Model Publication No. 2-58401 consists of a switch, a pressing member, and a presser. The switch is exposed on the control section. The pressing member is a waterproof film that has elasticity and shields the switch to keep the switch watertight. The presser that presses the switch is fixed to the pressing member and opposed to the switch.

In general, however, the external pressure of an endoscope is relatively higher than the internal pressure thereof after the endoscope undergoes a pressurization step or a dry step that is one step of autoclaving (sterilization with high-temperature high-pressure steam). Due to a difference in pressure between the interior of the endoscope and the exterior thereof, force works on the endoscope from the exterior of the endoscope to the interior thereof. In the endoscope described in the Japanese Unexamined Utility Model Publication No. 2-58401, the soft pressing member elastically deforms toward the interior of the endoscope. An end of the presser fixed to the pressing member approaches the switch. In some cases, the end of the presser may press the switch.

Moreover, if the end of the presser presses the switch to a great extent, a very small stem that forms the switch may deform permanently. In particular, at the pressurization step, not only a load derived pressure but also a thermal load derived from high temperature may be imposed on the switch. In some cases, therefore, the switch itself may deform.

Furthermore, after the dry step is completed, if the endoscope is left as it is for a prolonged period of time, force works on the endoscope from the exterior of the endoscope to the interior thereof for the prolonged period of time. Consequently, the stem may be deformed permanently. Eventually, when a user presses the push-button switch, the user may have a different sense of touch.

Moreover, an existing endoscope has elongated resin tubes incorporated in an insertion member thereof. The tubes are used as an aeration/perfusion channel, a therapeutic instrument passage channel, and others. When the endoscope is autoclaved, since the interior of the endoscope is sealed, if the resin tubes expand to increase their outer diameters due to pressure applied at the pressurization step, the other built-in components of the endoscope may be pressured. If one of the built-in components, for example, a light guide is pressured, such accident may happen that a fiber bundle over which illumination light is propagated is broken in the middle thereof.

There is a demand for an endoscope in which even if resin tubes expand at a pressurization step of autoclaving, the resin tubes do not pressure the other built-in components after completion of the autoclaving. Also demanded is an endoscope in which even if a flexible tube contracts to decrease its inner diameter due to pressure applied at a pressurization step, at least after the autoclaving is completed, resin tubes do not pressure the other built-in components. Also demanded is an endoscope in which resin tubes will not pressure the other built-in components even at the pressurization step.

Moreover, an existing endoscope has, for example, a soft breakage-of-insertion member preventing member engaged with the periphery of a flexible tube, which serves as part of the surface of a housing of the endoscope, in order to keep the flexible tube fluid-tight. In an atmospheric-pressure environment, fluid will not invade into the interior of the endoscope through the junction between the breakage-of-insertion member preventing member and flexible tube. When the endoscope is autoclaved, steam invades into the junction between the breakage-of-insertion member preventing member and flexible tube, and eventually into the interior of the endoscope because of pressure applied at a pressurization step.

At a dry step, on the other hand, the internal pressure of an autoclave is negative because of decompression. However, if the junction between the breakage-of-insertion member preventing member and flexible tube is kept fluid-tight, there is a fear that steam having invaded into the junction and the interior of the endoscope at the pressurization step may stagnate in the junction and the interior of the endoscope. In particular, if steam stagnates in the junction between the breakage-of-insertion member preventing member and flexible tube, a metallic part employed in the junction may corrode.

SUMMARY OF THE INVENTION

Accordingly, an object of the present invention is to provide an endoscope in which even if a pressing member is deformed due to autoclaving, the pressing member will not press a switch.

Another object of the present invention is to provide an endoscope whose switches are prevented from deforming due to autoclaving.

Still another object of the present invention is to provide an endoscope whose resin tubes will not pressure the other built-in components after completion of a pressurization step or a sterilization step that is one step of autoclaving.

Still another object of the present invention is to provide an endoscope in which a fluid-tight seal between an elastic member and the surface of the housing of the endoscope is freed at a dry step that is one step of autoclaving in order to prevent corrosion of the junction between the elastic member and the housing.

Briefly, an endoscope suitable for autoclaving in accordance with the present invention has a soft barrier that separates an interior from an exterior. When the barrier is located at a predetermined position, consideration is taken into a displacement of the barrier between the position of the barrier observed before start of autoclaving and the position thereof observed after completion of the autoclaving during which a load arising from predetermined pressure and a predetermined thermal load are imposed on the barrier. Therefore, even if the barrier is displaced, a member placed near the barrier is prevented from being broken due to the displacement.

DESCRIPTION OF THE PREFERRED EMBODIMENTS

Figure 1:
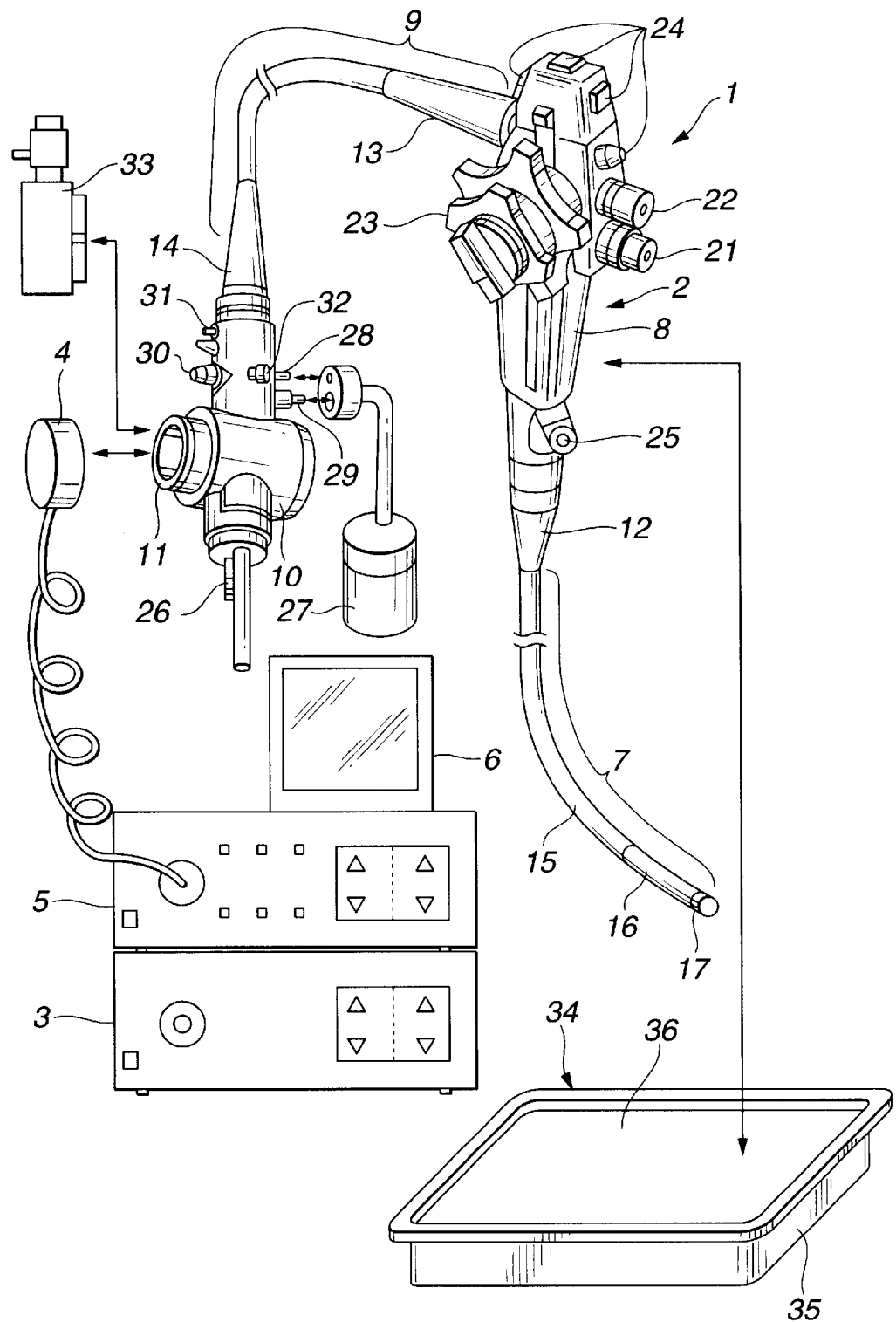
FIG. 1 is an explanatory diagram showing the configuration of an endoscope system.

Referring to the drawings, an embodiment of the present invention will be described below.

As shown in FIG. 1, an endoscope system 1 consists mainly of an endoscope 2, a light source apparatus 3, a video processor 5, and a monitor 6. The endoscope 2 is so constituted that can be cleaned and then sterilized with high-temperature high-pressure steam (hereinafter, autoclaved) after used for observation or operation.

The endoscope 2 has an imaging means that is not shown. The endoscope 2 can be detachably connected to the light source apparatus 3, whereby illumination light is propagated to a light guide that runs through the endoscope 2. The endoscope 2 and video processor 5 are connected over a signal cable 4. The video processor 5 controls the imaging means incorporated in the endoscope 2, processes a signal sent from the imaging means to produce a standard video signal, and transfers the video signal to the monitor 6. Consequently, an endoscopic image is displayed on the monitor 6.

The endoscope 2 consists mainly of an insertion member 7, a control section 8, a universal cord 9, and a connector unit 10. The insertion member is elongated and flexible. The control section 8 is fixed to the proximal end of the insertion member 7. The universal cord 9 having flexibility is extended from the lateral part of the control section 8. The connector unit 10 fixed to an end of the universal cord 9 is connected to the light source apparatus 3 so that it can be disconnected freely.

An electric connector 11 to or from which the signal cable 4 that is coupled to the video processor 5 can be freely coupled or uncoupled is formed on the lateral part of the connector unit 10.

An breakage-of-insertion member preventing member 12 including an elastic member is mounted on the joint between the insertion member 7 and control section 8 in order to prevent abrupt bending of the joint. Moreover, an breakage-of-control section preventing member 13 including an elastic member is mounted on the joint between the control section 8 and universal cord 9 in order to present abrupt bending of the joint. Furthermore, an anti-connector unit breakage member 14 including an elastic member is mounted on the joint between the universal cord 9 and connector unit 10 in order to prevent abrupt bending of the joint.

The insertion member 7 consists of a flexible tube 15, a bending section 16 distal to the flexible tube 15, and a distal part 17 distal to the bending section. The flexible tube 15 is a flexible soft member. The bending section 16 can be bent by manipulating an angling knob that will be described later and that is exposed on the control section 8. An observation optical system and an illumination optical system that are not shown are incorporated in the distal part 17.

The control section 8 has an aeration/perfusion button 21, a suction button 22, an angling knob 23, push-button switches 24, and a therapeutic instrument insertion port 25 and so on. The aeration/perfusion button 21 is used to perform aeration or perfusion. The suction button 22 is used to perform suction. The angling knob 23 is used to bend the bending section 16. The push-button switches 24 are a plurality of remote control switches used to remotely control the video processor 5. The therapeutic instrument insertion port 25 is an opening that opens into a therapeutic instrument channel.

An aeration/perfusion nozzle which is not shown and from which cleaning fluid or gas is jetted out to an observation window included in the observation optical system, which is not shown, during aeration or perfusion is placed in the distal part 17. Moreover, a suction port that is not shown and that is a distal opening of the therapeutic instrument channel that is not shown opens on the space in the distal part 17. A therapeutic instrument is passed through the therapeutic instrument channel formed in the insertion member 7 or fluid is sucked from a body cavity through the therapeutic instrument channel formed therein. Moreover, a fluid supply port which is not shown and through which fluid is jetted out opens toward an object of observation.

The connector unit 10 has an air supply base 26, a water supply tank pressurization base 28, a fluid supply base 29, a suction base 30, and an injection base 31. The air supply base 26 is connected to an air source, which is not shown and incorporated in the light source apparatus 3, so that it can be disconnected freely. The water supply tank pressurization base 28 and fluid supply base 29 are connected to a water tank 27, which is a fluid source, so that they can be disconnected freely. The suction base 30 is connected to a suction device that is not shown and that sucks fluid through the suction port in the distal part 17. The injection base 31 is connected to a water source that is not shown and that supplies water through the fluid supply port present in the distal part 17.

Moreover, the connector unit 10 has a ground base 32 through which high-frequency leakage current is fed back to a diathermy device if the leakage current flows through the endoscope during diathermy.

The electric connector 11 has an air vent hole that is not shown and that links the interior of the endoscope 2 and the exterior thereof. Moreover, a pressure regulating valve-inclusive waterproof cap 33 is freely detachably attached to the electric connector 11. The waterproof cap 33 has a pressure regulating valve that is not shown and that serves as a linking means. The pressure regulating valve opens when the internal pressure of the endoscope 2 is higher than the external pressure thereof. When the external pressure of the endoscope 2 is higher than the internal pressure, the pressure regulating valve is closed in order to keep the interior of the endoscope 2 fluid-tight and shut out the interior thereof from the exterior thereof.

For autoclaving, the endoscope 2 is stowed in a sterilization casing (hereinafter, casing) 34.

The casing 34 consists of a tray 35 in which the endoscope 2 is stowed and a lid member 36 that covers the tray 35. Each of the tray 35 and lid member 36 has a plurality of pores that are not shown. During autoclaving, steam passes through the pores.

The tray 35 has a restriction dent, which is not shown and shaped in conformity with the endoscope 2, formed therein. The components of the endoscope 2 are settled in predetermined places in the restriction dent. The restriction dent includes an insertion-member restriction dent which is not shown and in which the insertion member 7 having flexibility is fitted.

Typical conditions for autoclaving are stipulated in the U.S. standard ANSI/AAMI ST37-1992 recommended by the American National Standards Institute and published from the Association for the Advancement of Medical Instrumentation. The standard stipulates that, for example, a pre-vacuum sterilization process should be performed at 132° C. for 4 min and a gravity settling sterilization process should be performed at 132° C. for 10 min.

The condition of the temperature for autoclaving varies depending on the model of an autoclave or the time required for the autoclaving. Generally, the temperature for autoclaving ranges from about 115° C. to about 138° C. Some types of autoclaves can be set to about 142° C. The time required for autoclaving varies depending on the condition of the temperature for autoclaving. Generally, the time ranges from about 3 min to about 60 min. Some types of autoclaves can be set to about 100 min.

The pressure in a sterilization chamber for autoclaving is generally set to a value that deviates from the atmospheric pressure by about +0.2 [MPa].

A general pre-vacuum high-temperature high-pressure steam sterilization process includes a pre-vacuum step and a sterilization step. At the pre-vacuum step, a sterilization chamber in which equipment to be sterilized is put is decompressed in preparation for sterilization. At the sterilization step succeeding the pre-vacuum step, high-pressure high-temperature steam is fed to the sterilization chamber for the purpose of sterilization.

The pre-vacuum step is needed in order to infiltrate steam into every corner of equipment to be sterilized at the succeeding sterilization step. When the sterilization chamber is decompressed, high-pressure high-temperature steam permeates the whole equipment to be sterilized. The pressure in the sterilization chamber for the pre-vacuum step is generally set to a value that deviates from the atmospheric pressure by a value ranging from about −0.07 [MPa] to about −0.09 [MPa].

Some sterilization processes include a dry step. At the dry step succeeding the sterilization step, the sterilization chamber is decompressed again in order to dry the sterilized equipment to be sterilized. At the dry step, the sterilization chamber is decompressed in order to eliminate steam from the sterilization chamber. This facilitates drying of the equipment to be sterilized placed in the sterilization chamber. The pressure in the sterilization chamber for the dry step is generally set to a value that deviates from the atmospheric pressure by a value ranging about −0.07 to −0.09 [MPa].

When the endoscope 2 is autoclaved, the pressure regulating valve-inclusive waterproof cap 33 is attached to the electric connector 11. In this state, the pressure regulating valve, which is not shown, of the waterproof cap 33 is closed. Namely, the air vent hole is blocked by the waterproof cap 33, and the interior of the endoscope 2 is sealed to be watertight and shut out from the exterior thereof.

When a sterilization process includes the pre-vacuum step, the pressure in the sterilization chamber is decreased at the pre-vacuum step. Consequently, a difference in pressure occurs between the interior and exterior of the endoscope 2. Namely, the external pressure of the endoscope 2 gets lower than the internal pressure thereof. This causes the pressure regulating valve to open. The interior of the endoscope communicates with the exterior thereof through the air vent hole. Consequently, a large difference will not be produced between the internal pressure of the endoscope 2 and the pressure in the sterilization chamber. Consequently, the endoscope 2 is protected from being broken due to a difference in pressure.

When the sterilization chamber is pressurized at the sterilization step, if a difference in pressure occurs between the interior and exterior of the endoscope, that is, the external pressure of the endoscope 2 gets higher than the internal pressure thereof, the pressure regulating valve closes. Consequently, high-pressure high-temperature steam cannot actively invade into the interior of the endoscope 2 through the air vent hole via the waterproof cap 33. However, the high-pressure high-temperature steam gradually invades into the interior of the endoscope via a sheathing of the flexible tube or O rings. The sheathing is made of a high polymer material, while the O rings are made of a fluorocarbon rubber. The O rings serving as sealing means are included in joints which are integral parts of the housing of the endoscope 2.

Incidentally, pressure that is the sum of pressure released during decompression at the pre-vacuum step and pressure applied at the sterilization step works on the housing of the endoscope 2 from the exterior of the endoscope to the interior thereof.

When the sterilization step is succeeded by a decompression step, the pressure in the sterilization chamber is decreased at the decompression step. Consequently, a difference in pressure occurs between the interior and exterior of the endoscope 2, that is, the external pressure of the endoscope 2 gets lower than the internal pressure thereof. This causes the pressure regulating valve to open almost at the same time. Consequently, the interior of the endoscope 2 communicates with the exterior thereof through the air vent hole. Therefore, a large difference will not be produced between the internal pressure of the endoscope 2 and the pressure in the sterilization chamber. Thus, the endoscope 2 is protected from being broken due to a difference in pressure.

Thereafter, the internal pressure of the endoscope becomes equal to the external pressure thereof, and the pressure regulating valve closes. When the decompression step is completed, the pressure in the sterilization chamber is equal to the atmospheric pressure.

When all the steps of autoclaving are completed as mentioned above, pressure that equals pressure released at the decompression step works on the housing of the endoscope from the exterior of the endoscope to the interior thereof.

Finally, the waterproof cap 33 is detached from the electric connector 11. Consequently, the interior of the endoscope 2 communicates with the exterior thereof through the air vent hole. The internal pressure of the endoscope 2 becomes equal to the atmospheric pressure. Consequently, the endoscope 2 is unloaded from the pressure that has worked on the housing.

After autoclaving is completed as mentioned above, the endoscope 2 is reused for endoscopic examination.

Referring to FIG. 2A to FIG. 3B, the detailed structure of the push-button switches 24 included in the endoscope 2 capable of being autoclaved will be described below.

Figure 2A:
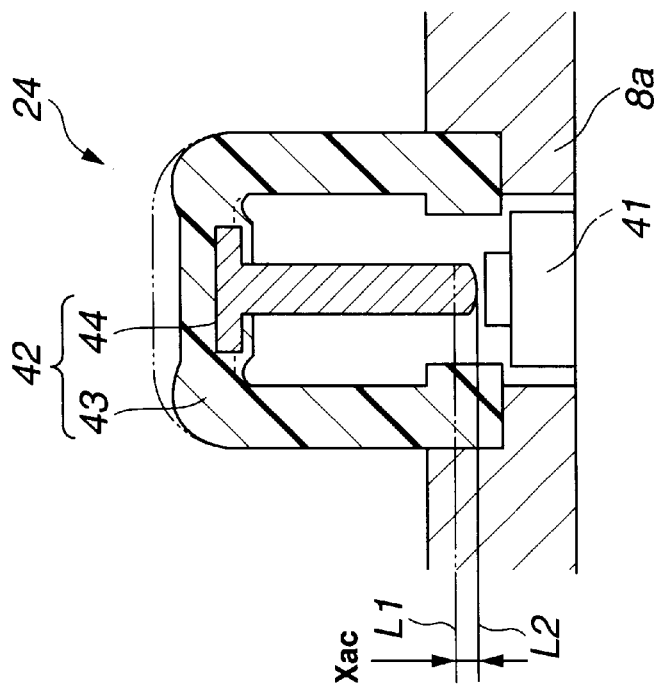
FIG. 2A is a cross sectional view showing a push-button switch under atmospheric pressure.
Figure 2B:
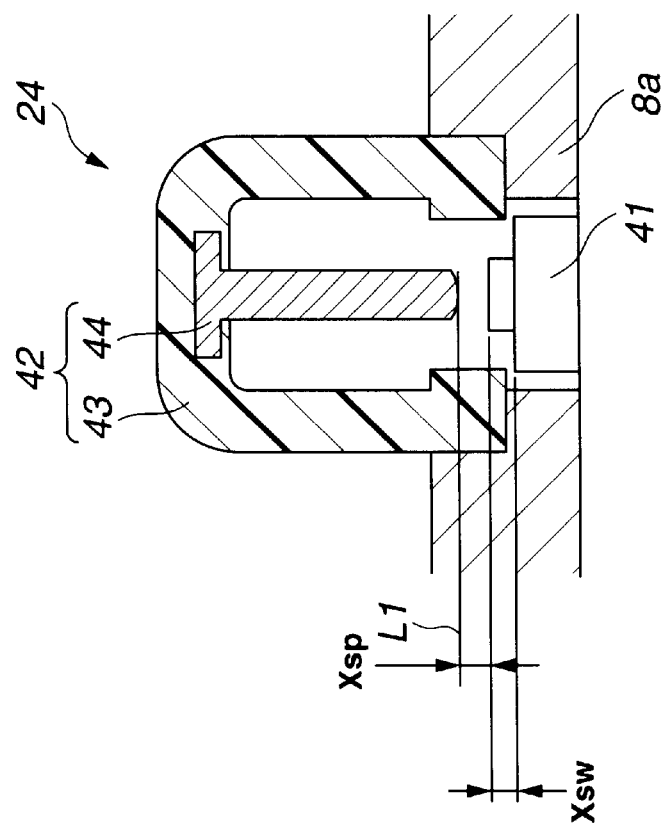
FIG. 2B is a cross sectional view showing the push-button switch that has undergone a pressurization step or dry step of autoclaving and that has entered a state different from the state shown in FIG. 2A.

As shown in FIG. 2A and FIG. 2B, each push-button switch 24 consists mainly of a switch 41 and a pressing member 42. The switch 41 can be sterilized with high-temperature high-pressure steam. The pressing member 42 covers the switch 41 to keep the switch 41 watertight, and includes a presser that will be described later. The pressing member 42 can elastically be deformed in order to actuate the switch 41, and can be displaced relative to the switch 41.

The pressing member 42 consists mainly of a waterproof film 43 and a presser 44. The waterproof film 43 serves as a barrier that can be elastically deformed when touched directly by an operator. The presser 44 is formed as an integral part of the waterproof film 43, and extended to face the switch 41 so that it can press the switch 41. The waterproof film 43 is fixed to a control section housing 8a that is an integral part of the control section 8 so that the waterproof film 43 will be kept fluid-tight.

A stem that is not shown is incorporated in the switch 41. When the stem deforms, the off and on states of the switch 41 are switched. The stem is made of a thin metal or a resin material so that the stem can be deformed easily. The waterproof film 43 is made of a soft rubber material. Moreover, the presser 44 is made of a hard metallic material or a resin material.

Figure 3A:
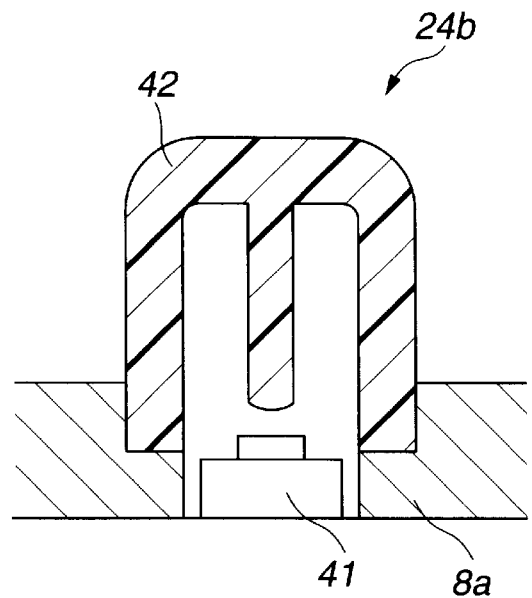
FIG. 3A is a cross sectional view for explaining the structure of a push-button switch whose waterproof film has the capability of a presser and which has the pressure thus formed as an integral part of a pressing member thereof.
Figure 3B:
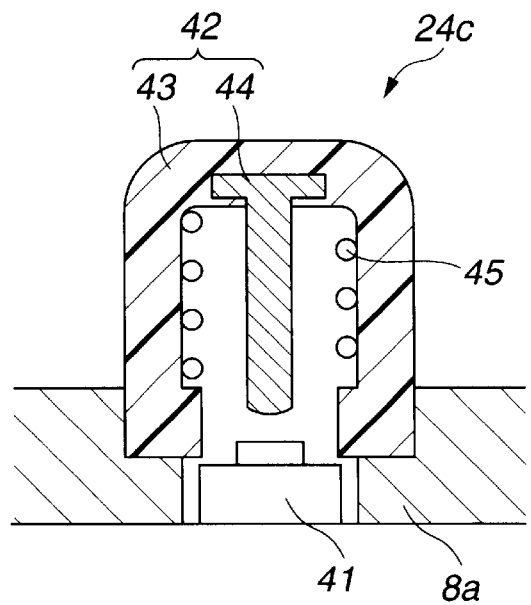
FIG. 3B is a cross sectional view of a push-button switch having an elastic member placed inside a waterproof film thereof.

The waterproof film 43 can be changed in shape such that, like a push-button switch 24b shown in FIG. 3A, the waterproof film 43 may have the capability of the presser 44. Thus, the pressing member 42 may be structured so that it will partly serve as the presser 44 and be devoid of the presser 44.

Elastic force exerted by the pressing member 42 included in the push-button switch 24 depends on the hardness of a rubber made into the waterproof film 43. Like a push-button switch 24c shown in FIG. 3B, for example, a coil spring 45 may be adopted as an elastic member and engaged with the inner surface of the waterproof film 43. Elastic force exerted by the coil spring may be thus utilized.

As shown in FIG. 2A, the position of an end of the presser 44 in an atmospheric-pressure environment shall be an initial reference position. A distance from a solid line L1 extended from the initial reference position to the top of the switch 41 shall be Xsp.

In FIG. 2A, Xsp may assume a positive value, that is, a gap may be present between the end of the presser 44 and the top of the switch 41, or Xsp may be zero. When Xsp is zero, it means that the end of the presser 44 is in contact with the top of the switch 41, or the presser 44 constrains the switch 41 to move inward. The switch 41 itself can move by a distance Xsw. That is to say, the distance Xsw is represented as a stroke of the switch 41.

After a pressurization step or a dry step of autoclaving is completed, the external pressure of the endoscope 2 is higher than the internal pressure thereof. Due to the difference in pressure between the interior of the endoscope and the exterior thereof, force works on the endoscope 2 from the exterior of the endoscope 2 to the interior thereof.

As shown in FIG. 2B, the soft waterproof film 43 elastically deforms inward or to the interior of the endoscope 2. Along with the elastic deformation, the end of the presser 44 moves by a distance Xac from the initial reference position indicated with an alternate long and two dotted chain line L1 to a position indicated with a solid line L2. The distance Xac is a displacement of the end of the presser 44 from the initial reference position.

Herein, the position of the end of the presser 44 observed before start of autoclaving shall be determined to meet Xac>Xsp. In this case, after the pressurization step or dry step of autoclaving is completed, the presser 44 keeps constraining the switch 41 to move inward. In particular, at the pressurization step, the stem that is not shown and incorporated in the switch 41 deforms permanently due to two loads; a load derived from pressure and a high-temperature thermal load. Consequently, at the time of endoscopic examination, there can be deterioration in the push-button switch manipulation or a conduction failure.

Moreover, after the dry step is completed, the presser 44 constrains the switch 41 to move inward for a longer time than it does when the push-button switch is manipulated normally. In other words, the switch 41 is put in a severer state than it is when the push-button switch is manipulated normally. Therefore, the stem that is incorporated in the switch 41 and not shown may be deformed permanently.

Moreover, depending on a resin material made into the pressing member 42, the pressing member 42 itself may deform permanently due to pressure applied at the pressurization step and a high-temperature thermal load imposed thereat. Because of the permanent deformation, even after autoclaving is completed, the presser 44 may keep constraining the switch 41 to move inward.

In consideration of the above fact, according to the present embodiment, the distance between the initial reference position observed in an atmospheric-pressure environment and the top of the switch 41 is determined to have a relationship expressed below:

$$Xac \leq Xsp \quad (1)$$

where Xac denotes a displacement of the end of the presser from the initial reference position, and Xsp denotes the distance between the initial reference position of the end of the presser and the top of the switch.

When the pressing member is positioned, consideration is taken into the position of the presser observed before start of autoclaving. Consequently, the presser can be surely prevented from constraining the switch to move inward due to pressure applied after completion of the pressurization step or dry step of autoclaving.

Incidentally, the displacement Xac of the pressing member 42 from the initial reference position thereof is a distance by which the pressing member 42 moves only due to pressure applied after completion of the pressurization step or dry step. Thus, when an operator who uses the endoscope 2 presses the waterproof film 43, the presser 44 can move by a distance Xsp+Xsw. At this time, the switch 41 is moved inward by the distance Xsw and thus moved normally.

Specifically, to begin with, an initial state attained before start of autoclaving will be discussed. In the initial state, the external pressure of the endoscope 2 and the internal pressure thereof are nearly equal to the atmospheric pressure (abbreviated as Pa). So, the pressure regulating valve incorporated in the endoscope 2 remains closed and a difference in pressure does not occur between the exterior of the endoscope 2 and the interior thereof. As a result, force oriented from the exterior of the endoscope to the interior thereof does not work on the endoscope 2. The waterproof film 43 does not therefore deform.

Next, the pre-vacuum step will be discussed.

At the pre-vacuum step, the internal pressure of an autoclave is negative (the negative pressure shall be abbreviated as −Pv1). At this time, a difference in pressure occurs between the exterior of the endoscope 2 and the interior thereof. Due to the difference in pressure, the pressure regulating valve opens and the internal pressure of the endoscope 2 is regulated. When the pre-vacuum step is completed, the difference in pressure between the exterior of the endoscope 2 and the interior thereof is nullified. In other words, the external pressure of the endoscope 2 and the internal pressure thereof become nearly equal to each other or become negative (the negative pressure is −Pv1). In this state, there is no difference in pressure between the exterior of the endoscope 2 and the interior thereof. and force oriented from the exterior of the endoscope to the interior thereof does not work on the endoscope 2. The waterproof film 43 does not therefore deform.

Next, the sterilization step will be discussed.

At the sterilization step, the interior of an autoclave is pressurized (the pressure shall be abbreviated as Pac). At this time, the external pressure of the endoscope 2 is Pac, and the internal pressure thereof is −Pv1. A difference in pressure therefore occurs between the exterior of the endoscope 2 and the interior thereof. The difference in pressure brings about force oriented from the exterior of the endoscope 2 to the interior thereof. The pressure regulating value therefore remains closed. In this state, the force arising from the difference in pressure (Pac-(−Pv1)) is applied to the waterproof film 43 of the push-button switch 24. As shown in FIG. 2B, the pressing member 42 is displaced by the distance Xac from the initial reference position thereof, and thus deformed.

According to the present embodiment, the relationship expressed as formula (1) is established for fear the pressing member 42 may constrain the switch 41 to move inward in the above state.

The dry step will be discussed below.

At the dry step, the internal pressure of the autoclave becomes negative (the negative pressure shall be abbreviated as −Pv2). At this time, the internal pressure of the endoscope 2 is also negative and about −Pv1.

Now, the absolute values of the pressures Pv1 and Pv2 will be described below.

The pressure Pv1 is the internal pressure of the endoscope 2 applied at the completion of the pre-vacuum step. The absolute value of the pressure Pv1 slightly decreases by the start of the dry step. This is because the O rings and other seals, which are not shown and are included in the endoscope 2, cannot keep the endoscope ideally absolutely airtight, and a pressure loss therefore occurs.

On the other hand, the pressure Pv2 is the negative pressure forcibly applied in the autoclave. The absolute values of the pressures Pv1 and Pv2 have the following relationship:

$$|Pv1| < |Pv2| \quad (2)$$

Consequently, the external and internal pressures of the endoscope 2 are negative. Due to a difference between the absolute values of the pressures, the pressure regulating valve opens and the external and internal pressures of the endoscope 2 are regulated. When the dry step is completed, there is no difference in pressure between the exterior and interior of the endoscope. Nearly equal negative pressure (the negative pressure shall be abbreviated as −Pav) is applied in the exterior and interior of the endoscope 2. In this state, since a difference in pressure does not occur between the exterior and interior of the endoscope 2, no force works on the endoscope 2 from the exterior of the endoscope 2 to the interior thereof. The waterproof film 43 does not therefore deform.

When the dry step is completed, the pressure in the autoclave becomes equal to the atmospheric pressure. At this time, the internal pressure of the endoscope 2 remains negative (the internal pressure is −Pavg). A difference in pressure therefore occurs between the exterior and interior of the endoscope 2. The difference in pressure brings about force oriented from the exterior of the endoscope 2 to the interior thereof. The pressure regulating valve therefore remains closed. In this state, the force arising from the difference in pressure (Pa-(−Pavg)) is applied to the waterproof film 43. Consequently, the waterproof film 43 deforms as shown in FIG. 2B.

However, the difference in pressure occurring at this time is smaller than the difference in pressure occurring at the sterilization step. The displacement of the pressing member 42 from the initial reference position thereof is smaller than Xac. Therefore, the pressing member 42 does not constrain the switch 41 to move inward in this state.

In general, at an institution at which the endoscope 2 is used, the endoscope 2 is usually not put in the autoclave until endoscopic examinations for a day are all completed. Autoclaving is started immediately after use of the endoscope. However, after the autoclaving is completed, the endoscope 2 is usually not taken out of the autoclave until the next morning. Consequently, the endoscope 2 retains in a state attained at completion of the dry step all night long at the longest. At this time, the internal pressure of the endoscope 2 remains negative. Pressure is kept applied to the waterproof film 43 all night long at the longest.

In a typical autoclave, pressure applied to the waterproof film 43 deviates from the atmospheric pressure by a value that falls within the range expressed below.

At the pressurization step:

$$Pac-(-Pv1)=\text{approx. }+0.27 \text{ to } +0.29 \text{ [MPa]} \quad (3)$$

At the dry step:

$$Pa-(-Pavg)=\text{approx. }+0.07 \text{ to } +0.09 \text{ [MPa]} \quad (4)$$

So, the distance Xsp and the hardness of a rubber made into the waterproof film 43 are set to values that disable the pressing member 42 from constraining the switch 41 to move inward when the pressing member 42 is moved with a load derived from, for example, 0.3 [Mpa] imposed on the waterproof film 43. At the same time, the values permit the pressing member to constrain the switch 41 to move inward when an operator presses the waterproof film 43 with his/her finger.

Since the endoscope 2 has the push-button switches 24 that are structured as mentioned above, advantages described below are provided.

After autoclaving is completed, even if the pressing member 42 is displaced toward the switch 41 and the waterproof film 43 is deformed permanently, the pressing member 42 will not constrain the switch 41 to move inward. Namely, the switch 41 will not be turned on and held down.

Moreover, after autoclaving is completed, the pressing member 42 will not constrain the switch 41 to move inward. So, even if the endoscope is left as it is for a prolonged period of time after being autoclaved, the stem incorporated in the switch 41 is prevented from permanently deforming. Consequently, a conduction failure is prevented from occurring, and a sense of touch is prevented from deteriorating.

Furthermore, when an autoclave is following the pressurization step, if the pressing member 42 does not constrain the switch 41 to move inward, the switch 41 is prevented from being broken due to a load derived from pressure at the pressurization step and a thermal load derived from high temperature thereat.

Moreover, even when an autoclave designed to follow the dry step is adopted, the initial reference position is determined so that the pressing member 42 will not constrain the switch 41 to move inward despite a difference in pressure occurring between the pressurization step and decompression step. Consequently, the switch 41 is prevented from being broken.

Incidentally, the distance Xsp between the initial reference position and the switch 41 observed before start of autoclaving, and the hardness of a rubber made into the waterproof film 43 may be set to values that permit the pressing member 42 to constrain the switch 41 to move inward after completion of the pressurization step or dry step. At this time, the values permit the pressing member 42 to constrain the switch 41 to move inward as long as constraining force exerted in constraining the switch 41 will not cause the stem incorporated in the switch 41 to permanently deform or break down.

In other words, after the pressurization step or dry step is completed, even if the pressing member 42 constrains the switch 41 to move inward, the stem incorporated in the switch 41 shall not permanently deform. The distance Xsp and the hardness of a rubber made into the waterproof film are set to values that meet the above condition and that establish the following relationship:

$$Xsp<Xac<Xsp+Xsw \quad (5)$$

where Xsp denotes the distance between the initial reference position of the end of the presser and the top of the switch, Xac denotes a displacement of the end of the presser from the initial reference position, and Xsw denotes a distance covered by one stroke of the switch.

Herein, a description will be made of the stem that is incorporated in the switch 41 and that will not permanently deform when the switch 41 is constrained to move inward by a distance Scr [mm].

In a typical autoclave, pressure applied to the waterproof film 43 deviates from the atmospheric pressure by a value expressed as formula (3) or (4).

In other words, when pressure deviating from the atmospheric pressure by 0.29 [Mpa] is applied to the waterproof film 43, the pressing member 42 shall deform and constrain the switch 41 to move inward by a distance shorter than Scr [mm].

As mentioned above, when a load derived from, for example, 0.29 [MPa] is imposed on the waterproof film 43, as long as the stem incorporated in the switch 41 does not permanently deform, the pressing member 42 may constrain the switch 41 to move inward after completion of the pressurization step or dry step.

The distance between the initial reference position and the switch 41 observed before start of autoclaving and the hardness of a rubber made into the waterproof film 43 are set to values that meet the above condition. At this time, the values permit the pressing member to constrain the switch 41 to move inward when an operator presses the waterproof film 43 with his/her finger.

Consequently, after the pressurization step or dry step is completed in the autoclave, force oriented from the exterior of the endoscope 2 to the interior thereof is applied because of a difference in pressure between the interior and exterior of the endoscope. The pressing member 42 moves toward the switch 41 and constrains the switch 41 to move inward. The magnitude of constraint is not so large as to permanently deform the stem incorporated in the switch 41.

Consequently, an operator is required to press the waterproof film 43 by a short distance. Thus, satisfactory manipulation is offered.

According to the present embodiment, consideration is taken into the pre-vacuum step or dry step at which the pressure in an autoclave is negative. Some types of autoclaves follow neither the pre-vacuum step nor the dry step.

When this type of autoclave is used, the external pressure of the endoscope 2 will not be lower than the internal pressure thereof. For this reason, the endoscope 2 need not necessarily have the pressure regulating valve. The endoscope 2 should merely be kept watertight and put in the autoclave.

Moreover, the interior of the autoclave is pressurized at the sterilization step (the internal pressure is Pac). The external pressure of the endoscope 2 is Pac, and the internal pressure thereof is Pa. This results in a difference (Pac−Pa) in pressure. At this time, force arising from the difference in pressure is applied to the waterproof film 43. In this case, the distance between the initial reference position and the switch 41 observed before start of autoclaving is set to a value dependent on the difference in pressure (Pac−Pa).

As far as a type of autoclave that follows neither the pre-vacuum step nor dry step is concerned, pressure applied to the waterproof film 43 deviates from the atmospheric pressure by a value expressed below.

At the pressurization step:

$$Pac-Pa=\text{approx. } +0.2 \, [MPa] \qquad (6)$$

At completion of the pressurization step:

$$Pa=\text{approx. } 0 \, [MPa] \qquad (7)$$

When an autoclave that follows neither the pre-vacuum step nor the dry step is used, the distance between the initial reference position and the switch 41 observed before start of autoclaving, and the hardness of a rubber made into the waterproof film 43 are set to values that disable the pressing member 42 from constraining the switch 41 to move inward. At this time, the values should disable the pressing member 42 from constraining the switch 41 to move inward when the pressing member 42 is displaced with a load derived from 0.2 [MPa] imposed on the waterproof film 43. Moreover, the values should permit the pressing member to constrain the switch 41 to move inward when an operator presses the waterproof film 43 with his/her finger.

Moreover, when the switch 41 itself makes a stroke (Xsw1) to enter the on state, the distance between the initial reference position and the switch 41 observed under the atmospheric pressure may be zero. In other words, the switch 41 itself may be displaced to physically make a stroke Xsw. In order to turn on the switch actually, the switch 41 must be pressed by a distance covered by the stroke Xsw1.

In this case, the distance between the initial reference position and the top of the switch 41 observed in an atmospheric-pressure environment is set to a value that has the following relationship:

$$Xac-Xsw1 \leq Xsp \qquad (8)$$

When the switch 41 makes the stroke (Xsw1) to enter the on state, before the endoscope is autoclaved, the pressing member 42 may constrain the switch 41 to move inward by a distance shorter than the distance covered by the stroke Xsw1.

Moreover, the present invention may be applied to a case where the pressing member 42 does not constrain the switch 41 to move inward during autoclaving as mentioned in relation to the foregoing embodiment. Alternatively, the present invention may be applied to a case where although the pressing member 42 constrains the switch 41 to move inward during autoclaving, the magnitude of constraint is not so large as to break the switch 41. In short, the distance between the initial reference position and the switch 41 obtained before start of autoclaving, and the hardness of a rubber made into the waterproof film 43 are set to values that disable the pressing member 42 from bringing the switch 41 to the on state. At this time, the values disable the pressing member 42 from bringing the switch 41 to the on state at any time when the endoscope 2 is reusable for examination after all the steps of autoclaving are completed.

If the distance between the initial reference position and the switch 41 observed before start of autoclaving and the hardness of a rubber made into the waterproof film 43 are set to values that disable the pressing member 42 from constraining the switch 41 to move inward at any step of autoclaving, no problem will occur. However, in this case, an operator must exert a large amount of force in manipulating the switch 41 during endoscopic examination. The operator is thus required to incur a load. An optimal relationship is therefore established according to a purpose or situation of use within the scope of the present invention.

Moreover, according to the present invention, the distance between the initial reference position and the switch observed before start of autoclaving, and the hardness of a rubber made into the waterproof film 43 are set to values that disable the pressing member 42 from constraining the switch 41 to move inward. At this time, the value disable the pressing member 42 from constraining the switch 41 to move inward even if pressure ranging from 0.07 [MPa] to 0.09 [MPa] works on the endoscope 2 from the exterior of the endoscope 2 to the interior thereof at the decompression step. When the distance and hardness are set to the values, after the autoclaving is completed, if the pressing member 42 is displaced toward the switch 41 for a prolonged period of time, the pressing member 42 will not constrain the switch 41 to move inward. Consequently, the switch 41 is prevented from being broken because it is constrained to move inward for a prolonged period of time. Moreover, after the pressing member 42 is displaced and cooled, even if the pressing member 42 is deformed, the pressing member 42 will not press the switch 41.

The present invention will not be limited to the aforesaid embodiment but various variants can be constructed without a deviation from the gist of the present invention.

Figure 4A:
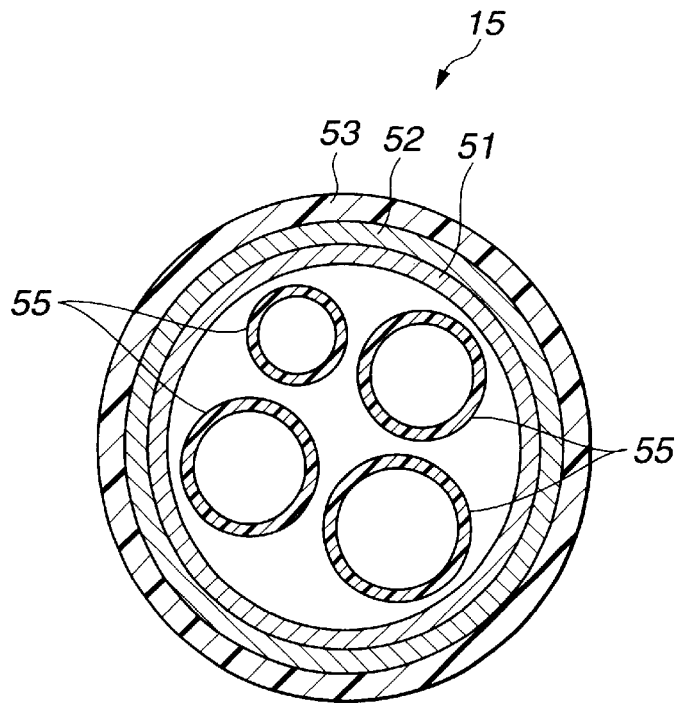
FIG. 4A is a cross sectional view showing a flexible tube in an initial state in which an endoscope is not yet put in an autoclave.
Figure 4B:
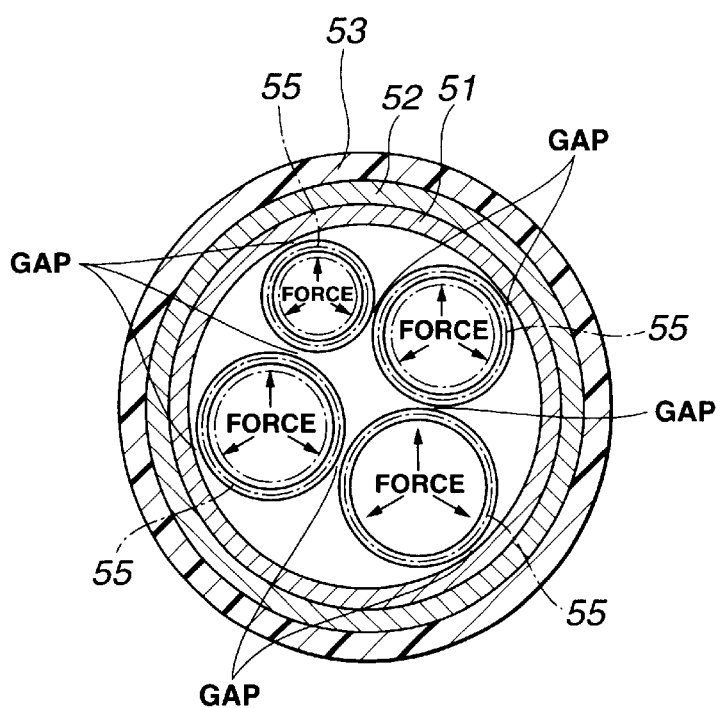
FIG. 4B is a cross sectional view showing the flexible tube in a state in which the external pressure of the endoscope that has been put in the autoclave with the flexible tube held in the state shown in FIG. 4A and that has undergone a sterilization step or a drying step is higher than the internal pressure thereof.

Referring to FIG. 4A and FIG. 4B, an example of a structure of the resin tubes incorporated in the flexible tube will be described below. The universal cord has the same structure as the flexible tube. Therefore, the resin tubes incorporated in the flexile tube will be solely described below. Dot-dash lines in FIG. 4B indicate the initial states of the resin tubes (denoted by 55).

As shown in FIG. 4A, the flexible tube 15 consists mainly of a spiral tube 51, a braid 52, and a sheathing 53 which are layered in that order from the innermost layer. The spiral tube 51 has a belt-like thin metallic piece spirally wound. The braid 52 covers the periphery of the spiral tube 51 and is made by plaiting metallic thin wires such as stainless steel wires in the form of a net. The sheathing 53 made of a resin covers the outer surface of the braid 52. Only one spiral tube 51 is depicted in FIG. 4A and FIG. 4B. Alternatively, the spiral tube 51 may be functionally two-ply or three-ply. Moreover, the sheathing 53 is made of a resin material, for example, an ester-series thermoplastic elastomer, an amide-series thermoplastic elastomer, a styrene resin, or a fluorocarbon rubber.

A plurality of channels including an aeration/perfusion channel used to perform aeration or perfusion and a therapeutic instrument passage channel that can also be used to perform suction is formed in the flexible tube 15. These channels are comprised of resin tubes 55 made of a resin material that is usually based on polytetrafluoroethylene (PTFE).

FIG. 4A and FIG. 4B show four resin tubes 55. Any number of resin tubes 55 may be incorporated, and the number of resin tubes 55 may be equal to or smaller or larger than four. Signal lines, a fiber bundle, metallic wires and the like are passed through the flexible tube 15, though they are not shown in FIG. 4A and FIG. 4B. Signals sent from an imaging device incorporated in the distal part 17 of the endoscope 2 are transmitted over the signal lines. Illumination light is propagated to an illumination lens incorporated in the distal part 17 over the fiber bundle such as a light guide. The metallic wires convey a manipulation that is performed on the control section 8 in order to angle the distal part 17.

As shown in FIG. 4A, in an initial state in which the endoscope 2 is not yet put in an autoclave, gaps are present among the resin tubes 55 and between the resin tubes 55 and the inner surface of the spiral tube 51 of the flexible tube 15.

When the endoscope 2 is autoclaved, after the sterilization step or dry step is completed, a difference in pressure occurs between the interior and exterior of the endoscope, and force works on the endoscope 2 from the exterior of the endoscope 2 to the interior thereof. Consequently, force works on the resin tubes 55 from the centers of the resin tubes to the peripheries thereof. This is because at least one end of each resin tube 55 opens on the space outside the endoscope 2. The force causes the resin tubes 55 to expand to increase their outer diameters.

After the sterilization step or dry step is completed, the resin tubes 55 expand to increase their outer diameters. The expansion of the resin tubes 55 arises from the difference in pressure between the exterior and interior of the endoscope 2. Normally, after the dry step is completed, the endoscope 2 is brought to an atmospheric-pressure environment, and the pressure regulating valve is opened forcibly. Thus, the expanded resin tubes 55 are restored to have their original outer diameters.

However, as far as an existing endoscope is concerned, the resin tubes 55 expand while placed in a high-temperature environment at the sterilization step. After the dry step is completed, even if the endoscope is brought to an atmospheric-pressure environment and the pressure regulating valve is forcibly opened, the resin tubes may not be restored to have their original outer diameters. The resin tubes may have their outer diameters held increased to be slightly larger than the original outer diameters.

According to the present embodiment, even after the sterilization step or dry step is completed, it should be so constituted that gaps are present among the resin tubes 55 and between the resin tubes 55 and the inner surface of the spiral tube 51.

Therefore, the sizes of the gaps among the resin tubes 55 observed in the initial state and the sizes of the gaps between the resin tubes 55 and the inner surface of the spiral tube 51 observed therein are set to values that permit gaps to lie, as shown in FIG. 4B, among the resin tubes 55 and between the resin tubes 55 and the inner surface of the spiral tube 51 even after completion of the sterilization step or dry step.

For setting the sizes of the gaps to the values, it is necessary to quantitatively grasp a magnitude of expansion by which the resin tubes 55 expand to increase their outer diameters after completion of the sterilization step or dry step. The magnitude of expansion is experimentally obtained by subjecting a unit resin tube 55 to the same difference in pressure as the difference in pressure occurring after completion of the sterilization step or dry step.

In a typical autoclave designed to perform decompression at the pre-vacuum step or dry step, pressure applied to the endoscope 2 from the exterior of the endoscope 2 to the interior thereof deviates from the atmospheric pressure by a value that falls within a following range:

At the pressurization step:

+0.27 to +0.29 [MPa]     (9)

At completion of the dry step:

+0.07 to +0.09 [MPa]     (10)

Consideration should therefore be taken into a case where the applied pressure is higher than the atmospheric pressure. For example, pressure that is higher than the atmospheric pressure by 0.3 [MPa] is applied to the unit resin tube 55 from the center of the tube to the periphery thereof, and a magnitude of expansion caused by the application of the pressure can be measured. In consideration of the magnitude of expansion, the sizes of the gaps present in the initial state are set to values that permit presence of gaps even after completion of the sterilization step or dry step.

Some types of autoclaves are designed to follow neither the pre-vacuum step nor the dry step. In such an autoclave, pressure working on the endoscope 2 from the exterior of the endoscope 2 to the interior thereof deviates from the atmospheric pressure by a value presented below.

At the pressurization step: +0.2 [MPa]

At completion of the pressurization step: 0 [MPa] Consideration is therefore taken into a case where the applied pressure is higher than the atmospheric pressure. For example, pressure higher than the atmospheric pressure by 0.2 [MPa] is applied to the unit resin tube 55 from the center of a unit resin tube 55 to the periphery thereof, and a magnitude of expansion caused by the application of the pressure is measured. In consideration of the magnitude of expansion, the gaps present in the initial state are set to proper values.

Moreover, normally, pressure higher than the atmospheric pressure by 0.3 [MPa] is applied to perform a test and a magnitude of expansion caused by the application of the pressure is taken into account in order to set the gaps present in the initial state to proper sizes, so that any autoclave could be used to sterilize the endoscope 2.

Consequently, even after the sterilization step or dry step is completed, gaps are present among the resin tubes 55 and between the resin tubes 55 and the inner surface of the spiral tube 51. When the flexible tube 15 is bent, the resin tubes 55 can freely move in the longitudinal direction of the flexible tube 15. No load is therefore imposed on fixtures attached to the ends of the resin tubes 55. Even when the resin tubes 55 expand, the other built-in components is prevented from being pressured.

Consequently, an occurrence rate of a defect such as water leakage derived from breakage of the fixture attached to the end of any resin tube can be reduced. Moreover, the other built-in components will not be broken.

According to the aforesaid embodiment, the sizes of the gaps present in the initial state are set to proper values in consideration of a magnitude of expansion by which the resin tubes 55 expand after completion of the sterilization step or dry step. Some types of flexible tubes 15 may contract to decrease their inner diameters after completion of the sterilization step or dry step. Consideration is therefore taken into not only the magnitude of expansion by which the resin tubes 55 expand at completion of the sterilization step or dry step but also a magnitude of contraction by which the flexible tube 15 contracts to decrease its inner diameter after completion of the sterilization step or dry step when the initial state is set to proper value.

In order to set the sizes of the gaps present in the initial state to proper values, consideration must be taken into the magnitude of expansion by which the resin tubes 55 expand to increase their outer diameters after completion of the sterilization step or dry step, and the magnitude of contraction by which the flexible tube 15 contracts to decrease its inner diameter. The magnitude of contraction is obtained experimentally similarly to the magnitude of expansion by which the resin tubes 55 expand to increase their outer diameters at completion of the sterilization step or dry step. Specifically, an experiment is performed to measure the magnitude of contraction by subjecting a unit flexible tube 15 to the same difference in pressure as the difference in pressure occurring at completion of the sterilization step or dry step.

In a typical autoclave, pressure applied to the endoscope 2 from the exterior of the endoscope 2 to the interior thereof deviates from the atmospheric pressure by a value expressed with formula (9) or (10).

Consideration is therefore taken into a case where the applied pressure is higher than the atmospheric pressure. For example, pressure higher than the atmospheric pressure by 0.3 [MPa] is applied to the unit flexible tube 15 from the exterior of the unit flexible tube 15 to the interior thereof. A magnitude of contraction by which the flexible tube contacts at that time is measured. In consideration of the magnitude of contraction, the sizes of the gaps present in the initial state are set to values that permit presence of gaps among the built-in components even after completion of the sterilization step or dry step.

Even for a type of autoclave designed to omit the prevacuum step and dry step, the magnitude of expansion obtained experimentally using a unit resin tube 55 is applied.

Moreover, in the aforesaid embodiment, the sizes of the gaps among the resin tubes 55 and the gaps between the resin tube 55 and the inner surface of the spiral tube 51 which are observed in the initial state are set to values that permit presence of gaps among the resin tubes 55 and between the resin tubes 55 and the inner surface of the spiral tube 51 after completion of the sterilization step or dry step.

However, gaps must be present among the resin tubes 55 and between the resin tubes 55 and the inner surface of the spiral tube 51 even after completion of the dry step. At the sterilization step, gaps may not necessarily be present as long as the other built-in components will not be broken.

At the sterilization step, as long as the resin tubes 55 and the other built-in components are not pressured to be broken, they may deform a bit. However, gaps must be present among the resin tubes 55 and between the resin tubes 55 and the inner surface of the spiral tube 51 after completion of the dry step. The sizes of the gaps among the resin tubes 55 and between the resin tubes 55 and the inner surface of the spiral tube 51 that are present in the initial state are set to values that permit presence of gaps among the resin tubes 55 and between the resin tubes 55 and the inner surface of the spiral tube 51 after completion of the dry step.

In a typical autoclave, pressure applied to the endoscope 2 from the exterior of the endoscope 2 to the interior thereof deviates from the atmospheric pressure by a value expressed in formula (9) or (10).

Consideration is therefore taken into a case where the applied pressure is higher than the atmospheric pressure. For example, pressure higher than the atmospheric pressure by 0.3 [MPa] is applied to a unit flexible tube 15 from the periphery of the tube to the center thereof. A magnitude of expansion of the resin tubes 55 and a magnitude of contraction of the flexible tube 15 that arise from the application of the pressure are then measured. At the same time, magnitudes of deformation by which the resin tubes and the other built-in components deform to break down are experimentally measured in advance. These magnitudes are taken account in order to set the sizes of the gaps present in the initial state to proper values.

The endoscope 2 may be transported after completion of the dry step. Therefore, when no gaps are present among the resin tubes 55 and between the resin tubes 55 and the inner surface of the spiral tube 51, if the insertion member 7 is bent during the transportation, the built-in components may be broken because they cannot move relative to one another. However, the endoscope 2 will not be moved at the sterilization step. Therefore, at the sterilization step, the resin tubes may deform a bit to have no gaps among them as long as they will not pressure the other built-in components.

In other words, when the sterilization step is under way in an autoclave, the resin tubes 55 expand, and no gaps are present among the resin tubes 55 and between the resin tubes 55 and the inner surface of the spiral tube 51. After completion of the dry step, gaps are present among the resin tubes 55 and between the resin tubes 55 and the inner surface of the spiral tube 51.

Consequently, no gaps are present at the sterilization step. However, after completion of the dry step, the internal pressure of the endoscope is retained at a negative value of −0.09 [MPa] at most owing to the operation of the pressure regulating valve. Even when the resin tubes 55 expand and the flexible tube 15 contracts, gaps are present among the resin tubes 55 and between the resin tubes 55 and the inner surface of the spiral tube 51. Even when the endoscope 2 is transported or manipulated anyhow, the endoscope 2 will not be broken.

Figure 5A:
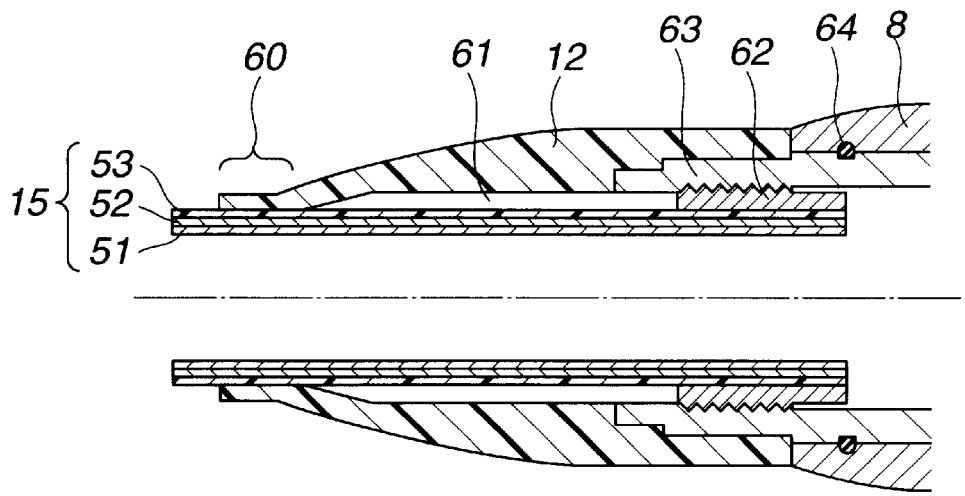
FIG. 5A is a longitudinal sectional view showing the state of a control section of the endoscope in an atmospheric-pressure environment.
Figure 5B:
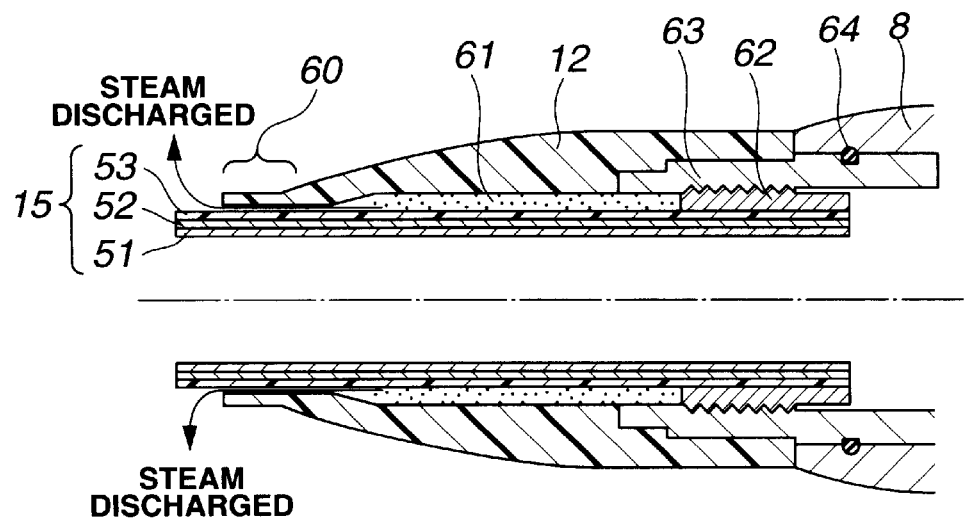
FIG. 5B is a longitudinal sectional view showing the state of the control section of the endoscope attained when the external pressure of the endoscope that has been put in the autoclave with the control section held in the state shown in FIG. 5A is lower than the internal pressure thereof.

Referring to FIG. 5A and FIG. 5B, an example of the structure of the breakage-of-insertion member preventing member will be described below.

The breakage-of-control section preventing member and breakage-of-connector unit preventing member have the same structure as the breakage-of-insertion member preventing member. The structure of the breakage-of-insertion member preventing member alone will be described, but the description of the other anti-breakage members will be omitted.

As shown in FIG. 5A, a seal portion 60 included in the endoscope 2 is engaged with the periphery of the flexible tube 15 in order to keep the flexible tube fluid-tight at least in an atmospheric-pressure environment. The inclusion of the seal portion 60 creates a space 61 between the breakage-of-insertion member preventing member 12 adjoining the control section 8 and the periphery of the flexible tube 15. The seal portion 60 is engaged with the periphery of the flexible tube 15 in order to keep the flexible tube 15 fluid-tight. At least in the atmospheric-pressure environment, fluid will not invade from the exterior of the endoscope 2 to the interior thereof.

In order to mechanically fix the breakage-of-insertion member preventing member 12 to the flexible tube 15, a connection pipe 62 and an insert member 63 are included. The connection pipe 62 is fixed to the sheathing 53 of the flexible tube 15 using an adhesive or the like. The insert member 63 is fixed to the breakage-of-insertion member preventing member 12 using an adhesive or the like, or molded as an integral part of the breakage-of-insertion member preventing member 12.

The connection pipe 62 and insert member 63 each have a screw threaded thereon so that they can be joined firmly. In general, the connection pipe 62 and insert member 63 are made of metallic materials. The insert member 63 is also engaged with the control section 8. A sealing member such as an O ring 64 is generally interposed between the insert member 63 and the control section 8.

In the course of cleaning an endoscope, the endoscope 2 may be immersed in a cleaning solution or water filled into a cleaning vessel that is not shown. In this case, pressure exerted by the cleaning solution or water works on the endoscope 2 from the exterior of the endoscope 2 to the interior thereof. However, the pressure is so negligible that the endoscope is held almost in the same state as the state shown in FIG. 5A.

In an environment in which the external pressure of the endoscope 2 is lower than the internal pressure thereof, force works on the endoscope 2 from the interior of the endoscope 2 to the exterior thereof. The force oriented from the interior of the endoscope 2 to the exterior thereof arises from pressure applied at the dry step of autoclaving. Pressure larger than the atmospheric pressure by a value ranging from 0.07 to 0.09 [MPa] works on the endoscope 2 from the interior of the endoscope 2 to the exterior thereof. Pressure that is higher than the atmospheric pressure by 0.05 [MPa] and oriented from the interior of the endoscope 2 to the exterior thereof brings about force smaller than the force oriented from the interior of the endoscope 2 to the exterior. When the pressure higher than the atmospheric pressure by 0.05 [MPa] works on the endoscope 2, the seal portion 60 separates from the periphery of the flexible tube 15. The inner diameter, thickness, and material of the seal portion 60 of the breakage-of-insertion member preventing member 12 are set to values that permit the separation of the seal from the periphery of the flexible tube. As the material of the seal portion 60, a resin material such as a fluorocarbon rubber is widely adopted.

When the endoscope 2 having the foregoing structure is autoclaved, the endoscope 2 is exposed to a high-temperature high-pressure steam environment at the sterilization step. Steam may infiltrate through the seal portion 60 and breakage-of-insertion member preventing member 12, and eventually invade into the space 61. However, when the pressure in the autoclave becomes negative at the dry step, the seal portion 60 of the breakage-of-insertion member preventing member 12 separates from the periphery of the flexible tube 15. The steam having invaded into the space 61 is effectively discharged to outside the endoscope 2.

Consequently, at the dry step of autoclaving, the steam having invaded into the space 61 is effectively discharged to outside. The connection pipe 62 and insert member 63 that are made of metallic materials will therefore not corrode.

According to the aforesaid embodiment, the inner diameter, thickness, and material of the seal portion 60 of the breakage-of-insertion member preventing member 12 are set to values that permit separation of the seal portion 60 from the periphery of the flexible tube 15 due to negative pressure occurring at the dry step of autoclaving.

However, some types of autoclaves are designed to omit the pre-vacuum step and dry step, that is, steps at which the pressure in the autoclave becomes negative. When such an autoclave is used to sterilize the endoscope 2, steam having invaded into the space 61 at the sterilization step will not be discharged. This leads to corrosion of the connection pipe 62 and insert member 63 that are made of metallic materials.

Therefore, the endoscope 2 is structured so that even when an autoclave designed to omit the dry step is used to sterilize the endoscope 2, steam having invaded into the space 61 can be discharged.

Specifically, the inner diameter, thickness, and material of the seal portion 60 of the breakage-of-insertion member preventing member 12 are set to values that permit separation of the seal portion 60 from the periphery of the flexible tube 15 when pressure higher than the atmospheric pressure by 0.05 [MPa] works on the endoscope 2 from the interior of the endoscope 2 to the exterior thereof.

Moreover, after the autoclaving is completed, the endoscope 2 has steam left in the space 61. The endoscope 2 is therefore put in a pressure container that is connected to a suction device capable of performing suction by means of pressure of 0.1 [MPa] or more. The pressure in the pressure container is set to a value that is smaller than the atmospheric pressure by 0.1 [MPa], that is, made negative.

The seal portion 60 is designed so that when pressure higher than the atmospheric pressure by 0.05 [MPa] works on the endoscope 2 from the interior of the endoscope 2 to the exterior thereof, the seal portion 60 will separate from the periphery of the flexible tube 15. As long as the pressure in the pressure container is set to the negative pressure, the seal portion 60 separates from the periphery of the flexible tube 15.

When the endoscope 2 having the aforesaid structure is autoclaved, the endoscope 2 is placed in a high-temperature high-pressure steam environment at the sterilization step. Steam may invade into the space 61 through the seal portion 60 and breakage-of-insertion member preventing member 12. In this case, when an autoclaving process devoid of the dry step is adopted, the steam is left intact in the space 61 at completion of autoclaving. However, thereafter, if the endoscope 2 is put in the pressure container that is set to the predetermined negative pressure, the seal portion 60 separates from the periphery of the flexible tube 15. Consequently, the steam having invaded into the space 61 at the sterilization step is discharged to outside.

The breakage-of-insertion member preventing member 12 is engaged with the periphery of the flexible tube 15 in order to keep the flexible tube 15 fluid-tight. Noted is that the present invention is not limited to the combination of the breakage-of-insertion member preventing member 12 and flexible tube 15. The present invention can apply to the combination of an elastic member having a seal portion and the surface of the housing of an endoscope.

Moreover, according to the present embodiment, an elastic member is engaged with the surface of the housing of an endoscope in order to keep the endoscope fluid-tight at least under the atmospheric pressure. Alternatively, the elastic member may be merely engaged with the surface of the housing of an endoscope but not be engaged therewith in order to keep he endoscope fluid-tight. However, the elastic member has a seal portion that keeps the endoscope fluid-tight when brought into close contact with the endoscope. In short, when the endoscope 2 is placed under predetermined pressure oriented from the inner surface of the endoscope 2 to the outer surface thereof, the elastic member separates from the surface of the housing of the endoscope. This allows discharge of steam that has invaded into a space between the elastic member and the surface of the housing of the endoscope at the sterilization step followed by an autoclave. Namely, the seal portion 60 is designed to separate from the surface of the housing of the endoscope 2.

According to the present invention, a wide range of different embodiments can be constructed based on the invention without a departure from the spirit and scope of the invention. Moreover, the present invention will be limited to the appended claims but not restricted to any specific embodiments.

What is claimed is:

1. An endoscope suitable for autoclaving comprising:
    a flexible tube that contracts to decrease its inner diameter when pressure or a thermal load is applied or imposed at a pressurization step of autoclaving; and
    a plurality of elongated resin tubes incorporated in the flexible tube that expand to increase their outer diameter when pressure or a thermal load is applied or imposed at the pressurization step of autoclaving;
    wherein gaps are set beforehand between the plurality of resin tubes and between each resin tube and an inner surface of the flexible tube so that such gaps will be present after completion of autoclaving between the plurality of resin tubes and between each resin tube and the inner surface of the flexible tube.

2. An endoscope according to claim 1,
    wherein the gaps will be present between the plurality of resin tubes and between each resin tube and the inner surface of the flexible tube even at the pressurization step of the autoclaving.

3. An endoscope according to claim 1, wherein the gaps will be present between the plurality of resin tubes and between each resin tube and the inner surface of the flexible tube even at a decompression step of the autoclaving.

4. An endoscope according to claim 1, wherein the gaps will be present between the plurality of resin tubes and between each resin tube and the inner surface of the flexible tube even if a difference in pressure occurring between the pressurization step of the autoclaving and a decompression step thereof functions on the resin tubes and the flexible tube.

5. An endoscope suitable for autoclaving comprising:

a flexible tube that contracts to decrease its inner diameter when pressure or a thermal load is applied or imposed at a pressurization step of autoclaving;

a plurality of elongated resin tubes incorporated in the flexible tube that expand to increase their outer diameter when pressure or a thermal load is applied or imposed at the pressurization step of autoclaving;

wherein gaps are set beforehand between the plurality of resin tubes and between each resin tube and an inner surface of the flexible tube so that such gaps will be present after completion of autoclaving between the plurality of resin tubes and between each resin tube and the inner surface of the flexible tube; and the gaps after the completion of autoclaving enable each resin tube to move freely in a longitudinal direction with respect to the resin tube when the flexible tube is bent.

6. An endoscope according to claim 5, wherein the gaps will be present between the plurality of resin tubes and between each resin tube and the inner surface of the flexible tube even at the pressurization step of the autoclaving, and the gaps at the pressurization step of the autoclaving enable each resin tube to move freely in the longitudinal direction when the flexible tube is bent.

7. An endoscope according to claim 5, wherein the gaps will be present between the plurality of resin tubes and between each resin tube and the inner surface of the flexible tube even at a decompression step of the autoclaving, and the gaps at the decompression step of the autoclaving enable each resin tube to move freely in the longitudinal direction when the flexible tube is bent.

8. An endoscope according to claim 5, wherein the gaps will be present between the plurality of resin tubes and between each resin tube and the inner surface of the flexible tube even if a difference in pressure occurring between the pressurization step of the autoclaving and a decompression step thereof functions on the resin tubes and the flexible tube, and the gaps at the decompression step of the autoclaving enable each resin tube to move freely in the longitudinal direction when the flexible tube is bent.

* * * * *